United States Patent
Rusu et al.

(10) Patent No.: US 10,357,180 B2
(45) Date of Patent: *Jul. 23, 2019

(54) HEALTH MONITORING SYSTEM

(71) Applicant: D.T.R. Dermal Therapy Research Inc., London (CA)

(72) Inventors: Ana Rusu, Sollentuna (SE); Saul Alejandro Rodriguez Duenas, Järfälla (SE); Stig Ollmar, Huddinge (SE)

(73) Assignee: D.T.R. Dermal Therapy Research Inc., London (CA)

( * ) Notice: Subject to any disclaimer, the term of this patent is extended or adjusted under 35 U.S.C. 154(b) by 321 days.

This patent is subject to a terminal disclaimer.

(21) Appl. No.: 14/157,309

(22) Filed: Jan. 16, 2014

(65) Prior Publication Data

US 2015/0196225 A1   Jul. 16, 2015

(51) Int. Cl.
*A61B 5/053* (2006.01)
*A61B 5/145* (2006.01)
(Continued)

(52) U.S. Cl.
CPC .......... *A61B 5/0538* (2013.01); *A61B 5/0031* (2013.01); *A61B 5/053* (2013.01);
(Continued)

(58) Field of Classification Search
CPC .................................................. A61B 5/00
(Continued)

(56) References Cited

U.S. PATENT DOCUMENTS 5,353,802 A * 10/1994 Ollmar ................. A61B 5/0531
600/547
5,581,248 A * 12/1996 Spillman, Jr. ............ G01D 5/48
340/870.31

(Continued)

FOREIGN PATENT DOCUMENTS

JP     2010-515492     5/2010
JP     2013-196184     9/2013

(Continued)

OTHER PUBLICATIONS

Muhammad Wager Hussain, "Low Power Implantable ASIC for Bio-Impedance Measurements—A Thesis submitted for the degree of Master of Science in System on Chip Design", Aug. 1, 2012, Retrieved from URL: http://www.diva-portal.org/smash/get/diva2:570016/FULLTEXT01.pdf.

(Continued)

*Primary Examiner* — May A Abouelela
(74) *Attorney, Agent, or Firm* — Santosh K. Chari; Blake, Cassels & Graydon LLP (57) ABSTRACT

The present invention relates to a health monitoring system comprising an implantable sensor configured to measure impedance within a body tissue of the subject resulting from an electrical current flowing through said body tissue, wherein the body tissue is sub-dermal or subcutaneous tissue of said subject, the sensor including a powering and communication circuit having a coil configured to be powered by an electromagnetic field and to communicate with external devices. Further, the system comprises a reader module including a coil configured to produce the electromagnetic field for powering the powering and communication circuit and for communicating with the powering and communication circuit, a computing device comprising a display device, a processing device and at least one storage device, the computing device being configured to communicate with (Continued)

other devices via at least one wireless network and a monitoring engine for determining or monitoring at least one physiological parameter based on measured impedance, wherein the reader module and the computing device and the monitoring engine are configured to communicate with each other.

13 Claims, 5 Drawing Sheets

(51) Int. Cl.
    A61B 5/1473    (2006.01)
    A61B 5/07      (2006.01)
    A61B 5/00      (2006.01)
    A61B 5/18      (2006.01)
    A61B 10/00     (2006.01)
    A61B 5/01      (2006.01)
    A61B 5/1455    (2006.01)

(52) U.S. Cl.
    CPC ........... A61B 5/0537 (2013.01); A61B 5/076 (2013.01); A61B 5/1473 (2013.01); A61B 5/14532 (2013.01); A61B 5/18 (2013.01); A61B 5/4833 (2013.01); A61B 5/7278 (2013.01); A61B 5/742 (2013.01); A61B 5/747 (2013.01); A61B 10/0012 (2013.01); A61B 5/0022 (2013.01); A61B 5/01 (2013.01); A61B 5/14539 (2013.01); A61B 5/14546 (2013.01); A61B 5/14551 (2013.01); A61B 5/413 (2013.01); A61B 5/4318 (2013.01); A61B 5/4878 (2013.01); A61B 2010/0019 (2013.01); A61B 2503/22 (2013.01); A61B 2560/0219 (2013.01)

(58) Field of Classification Search
    USPC .................. 600/547, 300, 301, 365; 329/304
    See application file for complete search history.

(56) References Cited

U.S. PATENT DOCUMENTS

| | | | |
|---|---|---|---|
| 5,833,603 A | 11/1998 | Kovacs et al. | |
| 5,970,986 A | 10/1999 | Bolz et al. | |
| 5,985,129 A | 11/1999 | Gough et al. | |
| 6,198,965 B1 | 3/2001 | Penner et al. | |
| 6,206,835 B1 | 3/2001 | Spillman, Jr. et al. | |
| 6,556,581 B1* | 4/2003 | He | H04L 25/20 370/419 |
| 8,204,603 B2 | 6/2012 | Maschino | A61N 1/0551 607/139 |
| 8,945,005 B2* | 2/2015 | Hafezi | A61B 5/073 340/572.1 |
| 2002/0042561 A1 | 4/2002 | Schulman et al. | |
| 2002/0128546 A1 | 9/2002 | Silver | |
| 2002/0155615 A1* | 10/2002 | Novikov | A61B 5/053 436/149 |
| 2004/0106380 A1* | 6/2004 | Vassiliou | H04B 17/14 455/73 |
| 2004/0127780 A1* | 7/2004 | Ollmar | A61B 5/0531 600/365 |
| 2004/0162501 A1* | 8/2004 | Imran | A61M 31/002 600/547 |
| 2004/0180391 A1 | 9/2004 | Gratzl et al. | |
| 2005/0137480 A1 | 6/2005 | Alt et al. | |
| 2006/0036286 A1 | 2/2006 | Whitehurst et al. | |
| 2006/0091944 A1* | 5/2006 | Kim | H03D 3/007 329/304 |
| 2007/0010759 A1 | 1/2007 | Parsonnet | |
| 2007/0161881 A1* | 7/2007 | Ollmar | A61B 5/053 600/347 |
| 2007/0270672 A1 | 11/2007 | Hayter | |
| 2007/0276201 A1 | 11/2007 | Lee et al. | |
| 2008/0075199 A1* | 3/2008 | Bengtson | H03F 3/189 375/316 |
| 2008/0126460 A1* | 5/2008 | Jiang | G01S 7/52028 708/317 |
| 2008/0219379 A1* | 9/2008 | Chrabieh | H04L 25/0226 375/298 |
| 2009/0143696 A1 | 6/2009 | Najafi et al. | |
| 2010/0100003 A1* | 4/2010 | Chetham | A61B 5/0537 600/547 |
| 2010/0292550 A1 | 11/2010 | Abrahamson et al. | |
| 2011/0028803 A1 | 2/2011 | Ollmar | |
| 2011/0082383 A1* | 4/2011 | Cory | A61B 5/0536 600/547 |
| 2011/0087129 A1* | 4/2011 | Chetham | A61B 5/053 600/547 |
| 2011/0208028 A1* | 8/2011 | Rossi | A61B 5/0537 600/372 |
| 2012/0109001 A1* | 5/2012 | Ellingson | A61N 1/08 600/547 |
| 2013/0241745 A1 | 9/2013 | Colvin, Jr. et al. | |
| 2014/0031713 A1* | 1/2014 | Gaw | A61B 5/0537 600/547 |
| 2014/0128722 A1* | 5/2014 | Schweitzer | A61B 5/7203 600/411 |

FOREIGN PATENT DOCUMENTS

| | | |
|---|---|---|
| WO | WO2009/121392 A1 | 10/2009 |
| WO | WO2012/076709 A1 | 6/2012 |
| WO | 2013/014671 A1 | 1/2013 |

OTHER PUBLICATIONS

International Search Report issued in PCT/EP2015/050486 dated Mar. 2, 2015.
Haider, Mohammad R. et al., "Low-Power Low-Voltage Current Readout Circuit for Inductively Powered Implant System", IEEE Transaction on Biomedical Circuits and Systems, vol. 4, No. 4, Aug. 2010, pp. 205-213.
Karacolak, Tutku et al., "Electrical Properties of Rat Skin and Design of Implantable Antennas for Medical Wireless Telemetry", IEEE Transactions on Antennas and Propagation, vol. 57, No. 9, Sep. 2009, pp. 2806-2812.
Lei, Ming et al., "A Hydrogel-Based Implantable Micromachined Transponder for Wireless Glucose Measurement", Diabetes Technology & Therapeutics, vol. 8, No. 1, 2006, pp. 112-122.
Nicolau Jr., Dan V. et al., "An Implantable Remote-Powered Optoelectronics Device for in vivo Spectral Analysis and Biochemical Tests", Proceedings of SPIE, vol. 5275, 2004, pp. 223-230.
Rai, Pratyush et al., "Wireless Glucose Monitoring Watch Enabled by an Implantable Self-Sustaining Glucose Sensor System", Proc. of SPIE, vol. 8548, 2012, pp. 85481G-1-85481G-8.
Shaul, Ozeri et al., "Non-invasive Sensing of the Electrical Energy Harvested by Medical Implants Powered by an Ultrasonic Transcutaneous Energy Transfer Link", IEEE, 2012, pp. 1153-1157.
Siley, Kanber Mithat et al., "Inductive Power Link for a Wireless Cortical Implant with Two-Body Packaging", IEEE Sensors Journal, vol. 11, No. 11, Nov. 2011, pp. 2825-2833.
Trung, N.T. et al., "Time Domain ADC for Blood Glucose Implant", Electronics Letters, Dec. 2011, pp. S18-S20.
Valdastri, Pietro et al., "Wireless Implantable Electronics Platform for Chronic Fluorescent-Based Biosensors", IEEE Transactions on Biomedical Engineering, vol. 58, No. 6, Jun. 2011, pp. 1846-1854.

* cited by examiner

HEALTH MONITORING SYSTEM

FIELD OF THE INVENTION

The present invention relates to a health monitoring system including an implantable sensor.

BACKGROUND OF THE INVENTION

Up to the present time, effective monitoring and follow-up of user related conditions or parameters such as different physiological parameters, health status, drug compliance has been limited to user's wearing implantable pacemakers and implantable cardioverters-defibrillators (ICDs). Current devices allow access to multiple critical data points reflecting device functionality and overall clinical condition of the user. The most recent advancements in device follow-up has provided for easier access to device stored data by utilizing wireless connectivity and internet based access to data as complement to information derived in point of care settings.

Nevertheless, despite these improvements in technology, there is a need of an improved system for effective monitoring and follow-up of user related conditions or parameters such as different physiological parameters including hydration, glucose levels etc., health status, drug compliance, in connection with organ transplantations to monitor the vitality of organs during transportation from donor to recipient, and to monitor signs or rejection, infections or ischemia, monitor the ovarian cycle using e.g. temperature, and monitoring glucose and hydration to identify alertness of aviators, truck drivers etc. There is clearly a need of such a system that can be used with implantable sensors that are small, reliable, easy and cheap to produce and that can be carried over extended periods of time without any need for re-charge or change of battery. Obviously, implantable pacemakers and implantable cardioverters-defibrillators (ICDs) are not suitable for such a system.

In addition, it would be very beneficial to include an implantable sensor in such improved system. Implantable sensors are sensors configured to be implanted within living tissue, e.g. within a living patient. The patient may comprise an animal or a human. Such implantable sensors are typically used to monitor one or more physiological parameters associated with the patient. For example, an implantable sensor may monitor a patient's blood or other body fluids for the presence or absence of a specific substance. Other implantable sensors may monitor the patient's body temperature. In general, implantable sensors may be used to provide valuable data that assists in diagnosing or treating an illness, or to help maintain or sustain a given level of physiological, chemical, or other activity or inactivity.

An area of high importance in which an implantable sensor and a monitoring system would be of great use is glucose monitoring or diabetes monitoring. At the present time, patients with diabetes rely on monitoring of blood glucose using an invasive blood glucose meter several times every day. Often this method involves drawing a small sample of blood, which is then tested directly for glucose level. There are numerous drawbacks to this method, for example, the patient have to draw samples of blood every day, several times a day at regular intervals, and there is some discomfort associated with drawing blood samples repeatedly. In addition, there is a margin of error, for example, the patient may forget to take a blood sample.

Present glucose sensors, which are typically used with some type of insulin-delivery system in order to treat diabetics, provide data needed to maintain the concentration of glucose within the patient at an acceptable level. Such glucose sensors must perform properly; otherwise, false data may be provided. Such false data (if acted upon) could result in the administration of an inappropriate amount of insulin, leading to death or serious injury. There is thus a critical need in the art for a sensor which is reliable and which can be monitored for proper function on a regular basis. Likewise, there is a need for a glucose sensor which must work properly within certain specific limits of accuracy.

Many implantable sensors require a power source, such as a battery, to power the sensor and transmitter and are therefore useful for only a limited period of time after implantation. After the on-board power source is depleted, an invasive operation, in addition to the initial implantation, will have to be made, if the device is to be removed or replaced.

Hence, there is also a need for an implantable device that can sense or detect one or more physiologic parameter values, and that can be remotely accessed by, for example, a hand held reader to obtain sensed parameters values in a non-invasive manner. No on-board power sources should be used so that the device will never need to be removed from an implantation site in order to replace an electrical power source, and can therefore remain implanted for an indefinite period of time.

In "Wireless Glucose Monitoring Watch enabled by an Implantable Self-sustaining Glucose sensor system" by Rai P. and Varadan V., Progress in Biomedical Optica and Imaging, Proceedings of SPIE8548, 2012, a system including an implantable glucose sensor that can be powered with inductive coupling is described. The sensor can communicate with a watch and glucose data can be displayed on the watch. The sensor described in this article has however only a limited working life since it consumes itself during use.

In Gupta et al, US2007276201, a system for monitoring strain as an indicator of biological conditions, such as spinal fusion, glucose levels, spinal loading, and heart rate is disclosed. The system includes an inter-digitated capacitance sensor, and RF transmitter, and an associated antenna, all of which are microminiature or microscopic in size and can be implanted in a biological host such as a human or animal. An inductively coupled power supply is also employed to avoid the need for implantation of chemical batteries. Power is provided to the sensor and transmitter, and data is transmitted from the sensor, when an external receiving device, such as a handheld RF ID type receiver, is placed proximate the location of the implanted sensor, transmitter and inductively coupled power supply. The implanted sensor, transmitter and inductively coupled power supply can be left in place permanently or removed when desired.

In Yang et al, US2004180391, in vivo or in vitro monitoring of chemical and biochemical species (e.g., pH, or glucose levels) in the interstitial fluid of patients or in a sample of a fluid to be analyzed is provided by a probe (10, 70, 210, 270). For in vivo monitoring, the probe is readily inserted by a minimally invasive method. Optical or electrochemical sensing methods are employed to detect a physical or chemical change, such as pH, color, electrical potential, electric current, or the like, which is indicative of the concentration of the species or chemical property to be detected. Visual observation by the patient may be sufficient to monitor certain biochemicals (e.g., glucose) with this approach. A CAP membrane allows high enzyme loadings, and thus enables use of microminiature probes, and/or diagnosis of low levels of the analyte(s), with sufficient signal-to-noise ratio and low background current.

In "A hydrogel-based implantable micromachined transponder for wireless glucose measurement" by Lei M. et al., Diabetes technology & Therapeutics, Vol. 8, No. 1, 2006, a hydrogel-based implantable wireless glucose sensor is described. The basic structure is a passive micromachined resonator coupled to a stimuli-sensitive hydrogel, which is confined between a stiff nanoporous membrane and a thin glass diaphragm.

In "Die Impedanzmessung zur Beurteilung von Ischämieschäden der humanen Leber in der Vorbereitung zur Transplantation", Gersing E., Langenbecks Arch Chir (1993) 378: 233-238, "Impedance spectroscopy on living tissue for determination of the state of organs", Gersing E., Bioelectrochemistry and Bioenergetics (1998) 45: 145-149, "Quantitative analysis of impedance spectra of organs during ischemia", Gheorghiu M, Gersing E, Gheorghiu E, Annals of the New York Academy of Sciences (1999) 873: 65-71, and "Messung der elektrischen Impedanz von Organen—Apparative Ausrustung fur Forschung and klinische Anwendung", Gersing E., Biomedizinische Technik (1991) 36: 6-11, impedance measurements in organ were studied.

To conclude, despite numerous attempts within the art, there is still a need of an improved system for effective monitoring and follow-up of user related conditions or parameters such as different physiological parameters including hydration, glucose levels etc., health status, drug compliance, in connection with organ transplantations to monitor the vitality of organs during transportation from donor to recipient, and to monitor signs of rejection, infections or ischemia, monitor the ovarian cycle using e.g. temperature, and monitoring glucose and hydration to identify alertness of aviators, truck drivers etc. Furthermore, there is still a need for an improved implantable sensor that is small, reliable, easy and cheap to produce and that can be carried over extended periods of time without need for re-charge or change of battery.

SUMMARY OF THE INVENTION

In accordance with broad aspects of the present invention, there is provided a health monitoring system including an implantable sensor for measuring or detecting one or more user related parameters, for example, physiologic parameters. The measured parameter can be remotely accessed by, for example, a hand held reader to obtain sensed parameters values in a non-invasive manner. The sensor does not use any on-board power sources and thus the sensor will never need to be removed from an implantation site in order to replace an electrical power source, and can therefore remain implanted for an indefinite period of time. Accordingly, the present invention provides for an effective monitoring and follow-up of user related conditions or parameters such as different physiological parameters including hydration, glucose levels etc., health status, drug compliance, in connection with organ transplantations to monitor the vitality of organs during transportation from donor to recipient, and to monitor signs of rejection, infections or ischemia, monitor the ovarian cycle using e.g. temperature, and monitoring glucose and hydration to identify alertness of aviators, truck drivers etc. In addition to monitoring of organs in the context of transplantation, from harvesting the organ from the donor to its implantation in the recipient, the present device could also be used to monitor the growth process of artificial organs, where the implanted sensor could be part of the matrix on which the artificial organ is grown, and stay as an integrated part of the full grown organ after implantation.

According to an aspect of the present invention, there is provided, a health monitoring system comprising an implantable sensor configured to measure impedance within a body tissue of the subject resulting from an electrical current flowing through said body tissue using a four-point measurement technology, wherein the body tissue is subdermal or subcutaneous tissue of said subject, the sensor including a powering and communication circuit having a coil configured to be powered by an electromagnetic field and to communicate with external devices. Further, the system comprises a reader module including a coil configured to produce the electromagnetic field for powering the powering and communication circuit and for communicating with the powering and communication circuit, a computing device comprising a display device, a processing device and at least one storage device, the computing device being configured to communicate with other devices via at least one wireless network and a monitoring engine for determining or monitoring at least one physiological parameter based on measured impedance, wherein the reader module and the computing device and the monitoring engine are configured to communicate with each other.

In embodiments of the present invention, there is provided a health care provider unit, wherein said communication device comprises a medical system communication engine configured to communicate with the health care provide server via at least one wireless network.

In embodiments of the present invention, there is provided a health care provider unit comprising a patient portal, wherein an authorized user can access patient information via the patient portal.

In embodiments of the present invention, the monitoring engine is implemented in the at least one storage device or the processing device of the computing device.

In embodiments of the present invention, the reader module is connectable to the computing device or is implemented in the computing device.

In embodiments of the present invention, there is provided the computing device configured to display the at least one physiological parameter on the display device.

In embodiments of the present invention, the monitoring engine comprises an alert function configured to provide at least one alert signal if at least one monitored physiological parameter satisfy predetermined conditions.

In embodiments of the present invention, the monitoring engine comprises an information provider module configured to obtain information related to the subject from at least one device via the at least one network and to present information related to the subject on the display device.

In embodiments of the present invention, the monitoring engine is configured to correlate the measured impedance with a predetermined relationship between impedance and at least one physiological parameter.

In embodiments of the present invention, the monitoring engine is configured to determine a glucose level in the subject by correlating the measured impedance with a predetermined relationship between impedance and blood glucose levels.

In embodiments of the present invention, the health monitoring system includes an implantable sensor comprising one pair of injection electrodes configured for injection of electrical current into the body tissue, wherein the electrical current is passed from one of the injection electrodes to the other of the injection electrodes through the body and one pair of sensing electrodes configured to detect the resulting voltage caused by the current flowing between the pair of injection electrodes and through said body tissue. The sensor further comprises a current signal output circuit operatively connected to the microcontroller and the injection electrodes and being configured to provide electrical current at predetermined frequencies to the injection electrodes, a detector operatively connected to the sensing electrodes and configured to receive the voltage detected by the sensing electrodes, wherein the detector is configured to measure the impedance of the body tissue based on the voltage detected by the pair of sensing electrodes, and a microcontroller operatively connected to the detector and being configured to receive impedance signals from the detector and to provide control signals to the current signal output circuit.

In embodiments of the present invention, the detector comprises an I/Q (In-phase/Quadrature) demodulator comprising one signal path for extraction of the I and Q components, respectively, wherein a sensed voltage is received from said sensing electrodes as input and an output of said I/Q demodulator is at least one DC signal.

In embodiments of the present invention, the powering and communication circuit is configured to communicate with the reading module using a back-scattering technique.

Due to its small size and the absence of a need of an on-board electrical power source, the sensor according to the present invention is particularly suitable for human implantation and can remain implanted for an indefinite period of time.

While a preferred sensor for use with the present invention comprises an implantable impedance sensor, or groups of impedance sensors, it is to be understood that the invention may include other types of implantable sensor(s) such as: temperature, pH, pO2 and other specific ions or molecules, local pressure (e.g. inside brain or scull).

The detector in the implantable sensor has one path to extract the I and Q components of the signal. The result of the I/Q demodulation is a DC signal, which entails that the extraction of the I and Q components can be performed when required. This is in contrast to prior art I/Q demodulation in communication systems, where phase and amplitude change over time and the processing therefore has to be performed in parallel. This solution leads to significant reduction in power consumption since only one path needs to be active. This is of very high importance in the present invention since limited power can be extracted from the inductive coupling. This also entails that sensor itself can be made smaller.

According to embodiments of the present invention, the device is configured to measure or monitor at least one physiological parameter of the body of the subject, wherein a monitoring engine is configured to correlate the measured impedance with a predetermined relationship between impedance and a at least one physiological parameter.

According to embodiments of the present invention, the microcontroller is operatively connected to the detector and being programmed to determine the physiological parameter in the subject by correlating the measured impedance with a predetermined relationship between impedance and levels of the at least one physiological parameter.

According to embodiments of the present invention, the microcontroller is programmed to determine a glucose level in the subject by correlating the measured impedance with a predetermined relationship between impedance and blood glucose levels.

According to embodiments of the present invention, the microcontroller is configured to communicate the measured impedance to an external device via the powering and communication circuit and wherein the monitoring engine is arranged in the external device.

According to embodiments of the present invention, the microcontroller is configured to communicate the measured impedance to an external device via the powering and communication circuit and wherein the monitoring engine is arranged in the external device and is configured to determine a glucose level in the subject by correlating the measured impedance with a predetermined relationship between impedance and blood glucose levels.

According to embodiments of the present invention, the at least one physiological parameter may include body temperature, hydration levels, hormone levels, lactate levels. It should be noted that these examples are non-exhaustive.

According to embodiments of the present invention, the current signal output circuit is configured to provide the injected current at a plurality of frequencies in a range between 1 kHz to 3 MHz, and preferably within a range between 1.5 kHz and 2.5 MHz, and more preferably in a range between 1.90 kHz and 2 MHz.

According to embodiments of the present invention, a frequency generation circuit operatively connected to the detector and being configured to generate reference signals having a frequency between 5 kHz to 50 MHz, and preferably in a range between 10 kHz to 20 MHz and more preferably in a range between 16 kHz to 16 MHz, and to deliver the reference signals to the detector.

According to embodiments of the present invention, the I/Q demodulator comprises a multiplier configured to multiply the received voltage with the reference signal.

According to embodiments of the present invention, the detector comprises a voltage amplifier for amplifying the voltage sensed by the sensing electrodes.

According to embodiments of the present invention, the detector further comprises a low pass filter for filtering the amplified signals.

According to embodiments of the present invention, the device is configured to be implanted within the body of the subject sub-dermally or subcutaneously.

While a preferred sensor for use with the present invention comprises an implantable impedance sensor, or groups of impedance sensors, it is to be understood that the invention may include other types of implantable sensor(s) such as: temperature, pH, pO2 and other specific ions or molecules, local pressure (e.g. inside brain or scull).

In yet another embodiment of the present invention, there is provided a device for measuring impedance in a subject, the device being configured to be implanted within the body of the subject and being configured to measure impedance within a body tissue of the subject resulting from an electrical current flowing through the body tissue using a two-point technology, wherein the body tissue is sub-dermal or subcutaneous tissue of the subject, comprising: one pair of injection electrodes configured for injection of electrical current into the body tissue, wherein the electrical current is passed from one of the injection electrodes to the other of the injection electrodes through the body; one pair of sensing electrodes configured to detect the resulting voltage caused by the current flowing between the pair of injection electrodes and through the body tissue, wherein the injection electrodes and the sensing electrodes are the same electrodes. Furthermore, the device comprises a current signal output circuit operatively connected to the microcontroller and the injection electrodes and being configured to provide electrical current at predetermined frequencies to the injection electrodes, a detector operatively connected to the sensing electrodes and configured to receive the voltage detected by the sensing electrodes, wherein the detector is configured to measure the impedance of the body tissue based on the voltage detected by the pair of sensing electrodes and a microcontroller operatively connected to the detector and being configured to receive impedance signals from the detector and to provide control signals to the current signal output circuit. A powering and communication circuit including a coil configured to be powered by an electromagnetic field produced by an external coil, the powering circuit being operatively connected to the microcontroller and configured to power the microcontroller, the current signal output circuit and the detector.

According another aspect of the present invention, there is provided a method for measuring impedance in a subject using a device being configured to be implanted within the body of the subject and being configured to measure impedance within a body tissue of the subject resulting from an electrical current flowing through the body tissue, wherein the body tissue is sub-dermal or subcutaneous tissue of the subject. The method comprises on a general level the following steps:

providing power for the impedance measurement by receiving power at a coil via an electromagnetic field produced by an external coil;

providing electrical current at predetermined frequencies to the injection electrodes;

injecting electrical current into the body tissue via one pair of injection electrodes, wherein the electrical current is passed from one of the injection electrodes to the other of the injection electrodes through the body;

sensing or detecting the resulting voltage caused by the current flowing between the pair of injection electrodes and through the body tissue at one pair of sensing electrodes; and measuring or determining the impedance of the body tissue based on the voltage detected by the pair of sensing electrodes.

According to embodiments of the method according to the present invention, an I/Q (In-phase/Quadrature) demodulation is performed in the step of measuring on one signal path for extraction of the I and Q components, respectively, wherein a sensed voltage is received from the sensing electrodes as input and an output of the I/Q demodulation is at least one DC signal.

According to embodiments of the method according to the present invention, the method further comprises determining or monitoring at least one physiological parameter of the body of the subject by correlating the measured impedance with a predetermined relationship between impedance and at least one physiological parameter.

According to embodiments of the method according to the present invention, the step of monitoring at least one physiological parameter comprises determining a glucose level in the subject by correlating the measured impedance with a predetermined relationship between impedance and blood glucose levels.

According to embodiments of the method according to the present invention, the method further comprises communicating the measured impedance and/or a determined value of the physiological parameter (such as a glucose level) to an external device via the coil using electromagnetic fields. If the measured impedance is communicated to the external device, the determination of the physiological parameter can be performed in the external device and the step of communicating is executed before the step of determining at least one physiological parameter.

According to embodiments of the method according to the present invention, the at least one physiological parameter include body temperature, hydration levels, hormone levels, lactate levels, pH, pO2, other specific ions or molecules, local pressure inside brain or scull According to embodiments of the method according to the present invention, the step of providing electrical current at predetermined frequencies to the injection electrodes comprises providing current for the injection electrodes at a plurality of frequencies in a range between 1 kHz to 3 MHz, and preferably within a range between 1.5 kHz and 2.5 MHz, and more preferably in a range between 1.90 kHz and 2 MHz.

According to embodiments of the method according to the present invention, further comprises generating reference signals having a frequency between 5 kHz to 50 MHz, an preferably in a range between 10 kHz to 20 MHz and more preferably in a range between 16 kHz to 16 MHz for the I/Q demodulation.

It is also to be understood that the principles underlying operation of an implantable sensor according to the present invention apply equally well to any sensor that is to remain unattended and submerged or immersed within a hostile environment, e.g. within a saline solution such as seawater, for a prolonged period of time. Thus, although the sensors described herein find particular applicability to sensors configured to be implanted within living tissue, and the description is directed to such implantable impedance sensors, the invention may also be applied to remote sensors of any kind that must be immersed unattended in a hostile environment for long periods of time.

The above-mentioned features and embodiments of the implantable medical device may be combined in various possible ways providing further advantageous embodiments.

Further advantageous embodiments of the device according to the present invention and further advantages with the present invention emerge from the dependent claims and the detailed description of embodiments.

As understood, there are a number of further application in which the present invention can be used.

For example, by measuring vaginal impedance of a woman, the fertility cycle could be monitored and a fertility status may be determined. It has be shown by Bartos L. "Vaginal impedance measurements used for mating in the rat", Laboratory Animals 1977; 11: 53-56, and in Bartos L, Sedlacek J., "Vaginal impedance measurements used for mating in the guinea-pig", Laboratory Animals 1977; 11: 57-58, that the vaginal impedance of rats discloses a sharp peak (or drop) at time of ovulation.

In embodiments of the present invention, the monitoring engine is configured to monitor the fertility cycle and determine a fertility status. For example, a sharp peak (or drop) in the vaginal impedance may indicate time of ovulation.

Moreover, glucose management or monitoring is also of high importance for athletes. The present invention may be very useful for athletes to monitor their glucose levels during, for example, exercise and competition.

Yet another application is to monitor hydration and glucose levels, for example, to detect or monitor diabetic hyperosmolar syndrome, which is a serious condition that develops when blood sugar reaches a very high level. At this level, the blood becomes thick and syrupy, causing diabetic hyperosmolar syndrome. Excess sugar passes from your blood into your urine, triggering a filtering process that draws tremendous amounts of fluid from your body. Diabetic hyperosmolar syndrome usually affects people with type 2 diabetes, and may develop in people who haven't yet been diagnosed with diabetes. Left untreated, diabetic hyperosmolar syndrome can lead to life-threatening dehydration. Prompt medical care is essential.

In addition to monitoring of organs in the context of transplantation, from harvesting the organ from the donor to its implantation in the recipient, the present device could also be used to monitor the growth process of artificial organs, where the implanted sensor could be part of the matrix on which the artificial organ is grown, and stay as an integrated part of the full grown organ after implantation.

According to a further aspect of the present invention, there is provided a device for measuring impedance in an object, the device being configured to be implanted within the object or attached to the object and being configured to measure impedance of the object resulting from an electrical current flowing through the body tissue, comprising one pair of injection electrodes configured for injection of electrical current into the object, wherein the electrical current is passed from one of the injection electrodes to the other of the injection electrodes through the object and one pair of sensing electrodes configured to detect the resulting voltage caused by the current flowing between the pair of injection electrodes and through the object. A current signal output circuit is operatively connected to the microcontroller and the injection electrodes and being configured to provide electrical current at predetermined frequencies to the injection electrodes and a detector operatively connected to the sensing electrodes and configured to receive the voltage detected by the sensing electrodes, wherein the detector is configured to measure the impedance of the object based on the voltage detected by the pair of sensing electrodes. A microcontroller operatively connected to the detector and being configured to receive impedance signals from the detector and to provide control signals to the current signal output circuit; and a powering and communication circuit including a coil configured to be powered by an electromagnetic field produced by an external coil, the powering circuit being operatively connected to the microcontroller and configured to power the microcontroller, the current signal output circuit and the detector. In embodiment of the present invention, the object is an organ intended for transplantation, or a section of the female reproductory tract.

Furthermore, edema such as pulmonary edema in patients suffering from heart diseases or pulmonary edema or cerebral edema in mountaineers during expeditions at high altitudes in order to monitor high altitude sickness or in divers to monitor divers sickness.

BRIEF DESCRIPTION OF THE DRAWINGS

The present invention will now be described, for exemplary purposes, in more detail by way of embodiments and with reference to the enclosed drawings, in which.

DETAILED DESCRIPTION OF EMBODIMENTS

Figure 1:
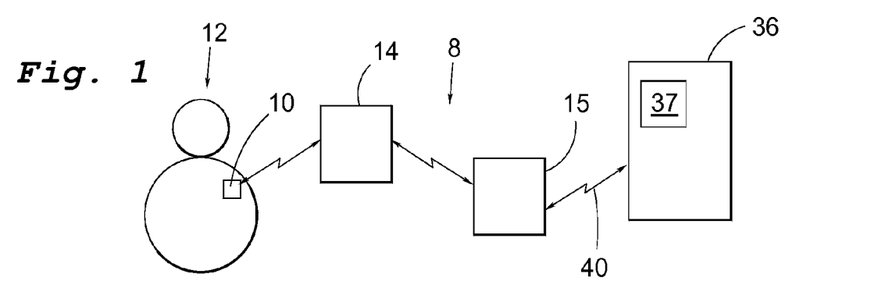
FIG. 1 is a schematic view of an embodiment of a system according to the present invention.

With reference first to FIG. 1, an embodiment of a system for measuring or monitoring user related conditions or parameters such as different physiological parameters including hydration, glucose levels etc., health status, drug compliance, in connection with organ transplantations to monitor the vitality of an organ during transportation from donor to recipient, and to monitor signs or rejection, infections or ischemia, monitor the ovarian cycle using e.g. temperature, and monitoring glucose and hydration to identify alertness of aviators, truck drivers etc. There is clearly a need of such a system that can be used with small, reliable, easy and cheap to produce and that can be carried over extended periods of time will be described. In preferred embodiments of the invention, the system uses a sensor that measures the impedance of body tissue and the impedance measurements are used to detect or monitor glucose levels.

A sensor 10 for measuring electrical bio-impedance of a subject 12 is implanted into the subject, for example subdermally or subcutaneously. The implantable sensor 10 according to the present invention will be described in detail below with reference to FIG. 6. The sensor 10 is powered by an external reader module 14 by using inductive coupling, for example, at frequencies around 10-15 MHz. The reader module 14 is capable of communicating with a microcontroller 61 of the sensor 10 (see e.g. FIG. 6). For example, the reader module 14 may be arranged to perform half-duplex back-scattering serial communication with the sensor 10, which also is known as impedance modulation or load modulation. This technique works by reflecting electromagnetic waves back to the source. The short distance relative to the wavelength means that the reflected wave is received almost instantly. Therefore instead of receiving a pulse back the mutual inductance behaves as a feedback loop and changes the apparent impedance of the inductor. The change in inductance will then change the current that passes through the coil. The changed current will then change the amplitude of the voltage over the coil, and the data can be treated as an amplitude modulated signal. In principle any method that changes the impedance in the secondary resonator can be used to transmit data. For example, amplitude modulation for the downlink (from the reader 14 to the implantable device or sensor 10) by changing the voltage that is available in the sensor 10. The uplink (from the implantable device 10 to the reader 14) uses load shift keying, where the quality factor of the load is changed according to the data being sent. The load is sensed by using a transformer (not shown), which senses the current that passes through the coil used to transmit power. An envelope detector (not shown) followed by a band pass filter (not shown) and comparator (not shown) is used to recover the data.

In embodiments of the present invention, the reader module 14 and the sensor 10 includes LRC resonant circuits configured for frequencies in a range between 10-15 MHz for power transmission and signal reception (at the reader 14). The reader module 14 is configured to communicate with a computing device 15, for example, using wireless communication including infrared, BLUETOOTH® wireless technology, 802.11a7b/g/n, cellular or other radio frequency communication systems.

Figure 2:
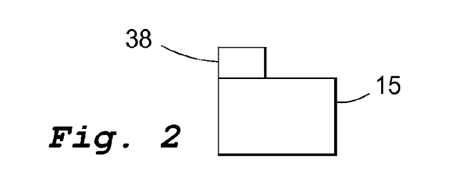
FIG. 2 is a schematic view of an embodiment of a computing device suitable for use in the system according to the present invention.

In embodiments of the present invention, the reader module is included in the computing device as shown in FIG. 2. For example, a reader module 38 may be connected or coupled to the computing device at a USB port of the computing device 15.

Figure 3:
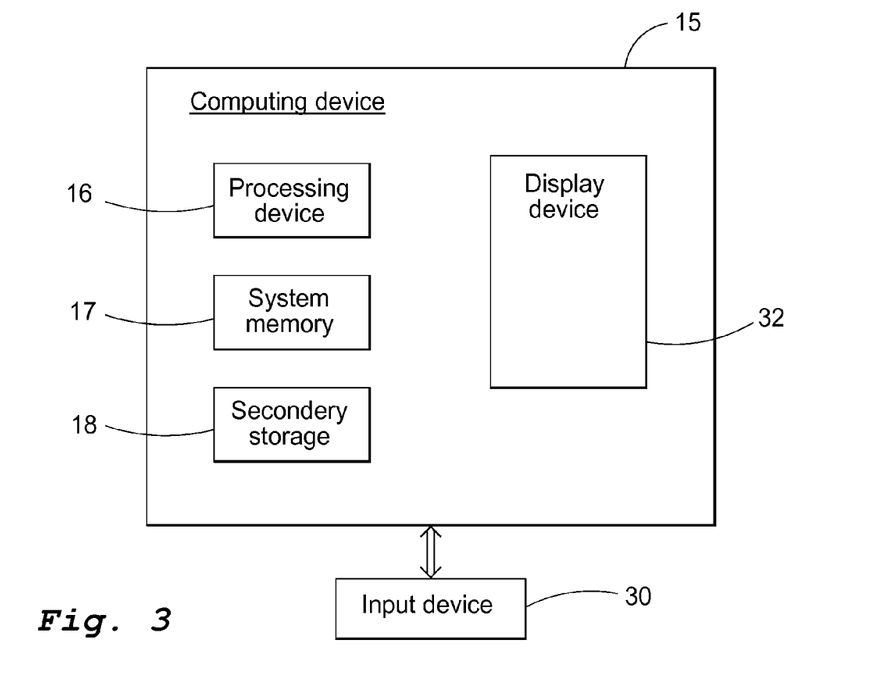
FIG. 3 is a schematic view of another embodiment of a computing device suitable for use in the system according to the present invention.

With reference to FIG. 3, the computing device 15 includes, in some embodiments, at least one processing device 16, such as a central processing device (CPU). A variety of processing devices are available from a variety a manufacturers, for example, Intel or Advanced Micro Devices. In this embodiment, the computing device also comprises a system memory 17.

Examples of computing devices suitable for use in the present system include, but without limitation to the mentioned examples, a desktop computer, a laptop computer, a tablet computer, a mobile computing device such as a smart phone (e.g. an iPhone® or a phone using Android OS), an iPod®, an iPad®, a mobile digital device or other mobile devices, or other devices configured to process digital instructions.

The system memory 17 includes read only memory and random access memory. A basic input/output system containing basic routines that act to transfer information within the computing device 15, such as start-up, is typically stored in the read only memory.

Further, the computing device 15 also includes a secondary storage 19 in some embodiments, such as a hard disk drive, for storing digital data. The secondary storage 19 and associated computer readable media provide non-volatile storage of computer readable instructions (including programs and program modules), data structures and other data for the computing device 15.

Although the exemplary environment described herein employs a hard disk drive and a secondary storage, other types of computer readable storage media are used in other embodiments. Examples of these other types of computer readable storage media include magnetic cassettes, flash memory cards, digital video disks, compact disc read only memories, digital versatile disk read memories, random access memories, or read only memories. Some embodiments include non-transitory media. Additionally, such computer readable storage media can include local storage or cloud-based storage.

Figure 4:
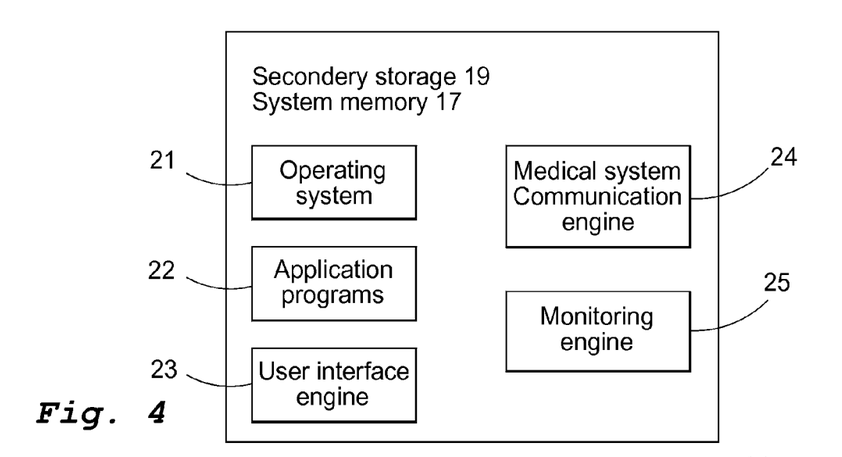
FIG. 4 is a schematic view of an embodiment of the computing device.

As illustrated in FIG. 4, a number of program modules can be stored in the secondary storage 19 and/or system memory 17 including an operating system 21, one or more application programs 22, a user interface engine 23, a medical system communication engine 24 and a monitoring engine 25. The computing device 15 can utilize any suitable operating system, such as Microsoft Windows™, Google Chrome™, Apple OS, Android OS, and any other operating systems suitable for a computing device. The monitoring engine may, in some embodiments, be arranged to determine or monitor a physiological parameter such as a glucose level based on measured impedance. In the embodiment shown in FIG. 2, the computing device is capable of determining or monitoring a physiological parameter such as glucose based on impedance measurements. The impedance measurements are performed by the sensor 10 and the impedance data is then transmitted to the reader module 14 via a powering and communication module 62 of the sensor (see FIG. 4).

In some embodiments, a user provides input to the computing device 15 through one or more input devices 30. Examples of input devices 30 include a keyboard, a mouse, a microphone, a touch sensor (such as a touchpad or touch sensitive display), an IR sensor or web-camera. The input device 30 is connected to the processing device 16 through an input/output interface that is coupled to a system bus (not shown).

In preferred embodiments of the present invention, the computing device 15 includes a display device 32 such as a monitor, liquid crystal display device, a projector or touch sensitive display device.

When used in a local area networking environment or a wide area networking environment (such as the Internet), the computing device 15 is typically connected to the network 40 (FIG. 1 and FIG. 2) through a network interface (not shown) such as an Ethernet interface. Other embodiments use other communication devices. For example, some embodiments of the computing device 15 include a modem for communicating across the network.

The computing device 15 is capable of communicating with, for example, a health care provide unit 36 via the network 40 using the medical system communication engine 24. The health care provider unit 36 comprises a patient portal 37, wherein an authorized user such as a medical doctor can access patient information via the patient portal 37. In embodiments of the present invention, the computing device 15 uploads information, for example, related to measure physiological parameters of the subject or patient to the health care provide unit 36. An authorized user, e.g. a medical doctor, can access the uploaded information via the patient portal 37. Other information such health status, drug compliance, etc. can also be uploaded to the health care provide unit from the computing device 15. An authorized user may also communicate with the patient via the patient portal 37, for example, send a prescription of a drug or send updated information related to health status of the patient. Other user related conditions or parameters such as different physiological parameters including hydration, glucose levels etc., health status, drug compliance, in connection with organ transplantations to monitor the vitality of an organ during transportation from donor to recipient, and to monitor signs of rejection, infections or ischemia, monitor the ovarian cycle using e.g. temperature, and monitoring glucose and hydration to identify alertness of aviators, truck drivers etc. can also be monitored or followed up in the present system 8.

Figure 5:
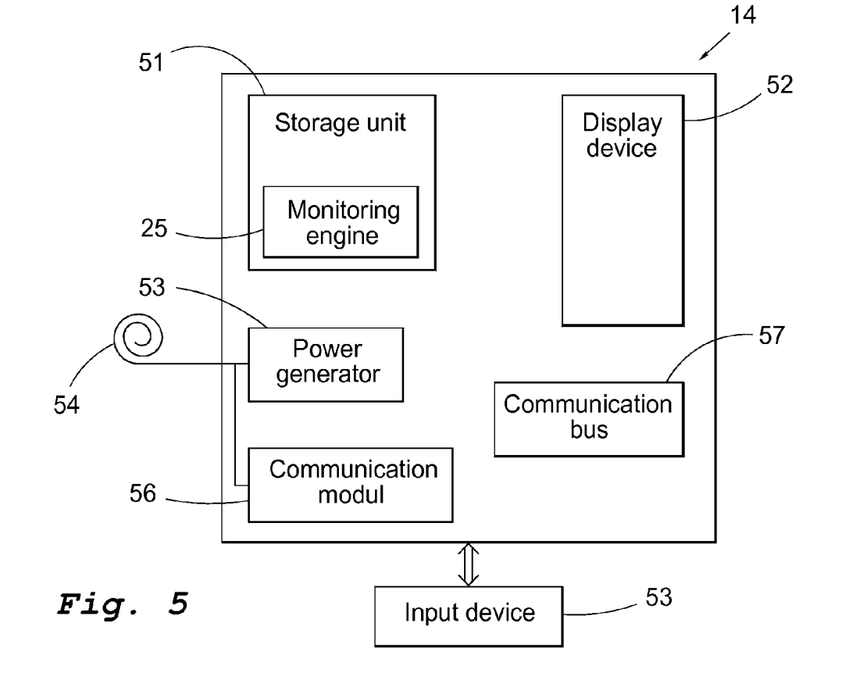
FIG. 5 is a schematic view of a reader module according to the present invention.

In embodiments of the present invention, the monitoring engine 25 may be included in a storage unit 51 of the reader module 14 as illustrated in FIG. 5, e.g. a read only memory and random access memory and a secondary storage such as a hard disk drive, for storing digital data. The secondary storage and associated computer readable media provide non-volatile storage of computer readable instructions (including programs and program modules), data structures and other data for the reader device. Although the exemplary environment described herein employs a hard disk drive and a secondary storage, other types of computer readable storage media are used in other embodiments. Examples of these other types of computer readable storage media include magnetic cassettes, flash memory cards, digital video disks, compact disc read only memories, digital versatile disk read memories, random access memories, or read only memories. Some embodiments include non-transitory media. Additionally, such computer readable storage media can include local storage or cloud-based storage.

The reader module 14 may also include devices such as a display device 52 such as a monitor, liquid crystal display device, a projector or touch sensitive display device and an input device 53 such as a keyboard, a mouse, a microphone, a touch sensor (such as a touchpad or touch sensitive display), an IR sensor or web-camera.

The reader module 14 further comprises a coil 54 for producing electromagnetic fields for powering the sensor 10. The coil 54 is connected to power generator 55 configured to generate the current and voltage for the electromagnetic field and a communication module 56 for receiving transmitted data from the sensor 10.

The reader module 14 may also comprise a communication bus 57 for connection to the computing device 15, for example, via direct connection via a USB port (as shown in FIG. 5) or wirelessly, for example, via IR communication or via BLUETOOTH®.

Figure 6:
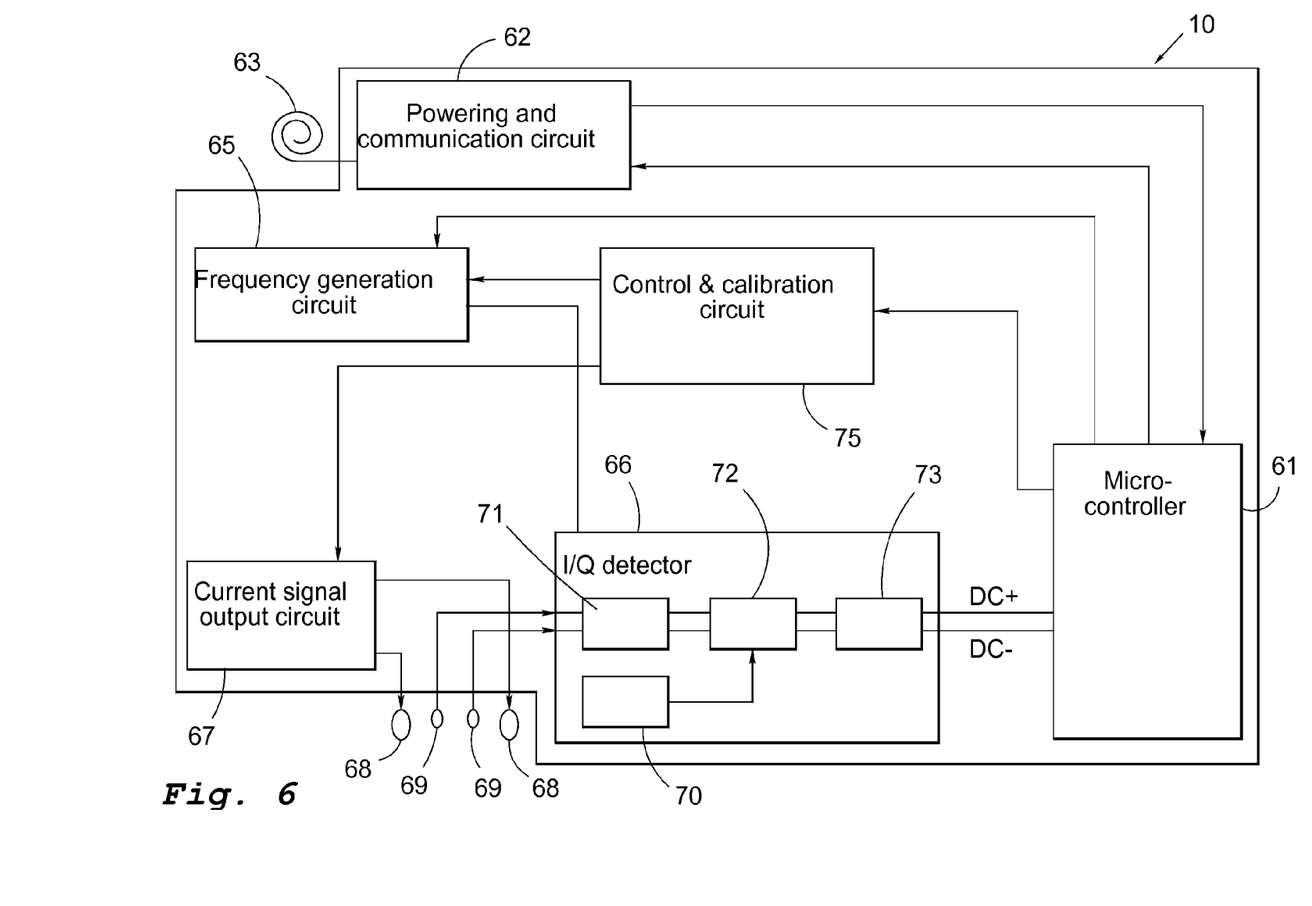
FIG. 6 is a schematic view of an embodiment of the implantable impedance sensor according to the present invention.

Turning now to FIG. 6, the implantable impedance device or impedance sensor will be discussed in more detail. FIG. 6 shows a block diagram of an embodiment of the sensor according to the present invention.

A powering and communication circuit 62 comprising analog circuits provides power to the sensor 10. The powering and communication circuit comprises a coil 63 for external powering by the reader module 14 using inductive coupling and the powering and communication circuit 62 is also configured to establish a communication mechanism with the reader module 14 using, for example, half duplex back-scattering serial technique. The powering and communication circuit 62 includes a full-wave rectifier circuit 64 which resonates with the coil 63, for example, at frequencies in a range between 10-15 MHz. The input to the powering and communication circuit 62 is an electromagnetic field produced by the coil 13 of the reading module 14. Output of the powering and communication circuit 62 is a DC voltage. The powering and communication circuit 62 is operatively connected to the microcontroller 61.

A frequency generation circuit 65 is configured to generate frequency reference clocks from signals having a frequency between 5 kHz to 50 MHz, and preferably in a range between 10 kHz to 20 MHz and more preferably in a range between 16 kHz to 16 MHz. These frequencies are used to generate sinusoidal current and I/Q waveforms for the I/Q impedance detection mechanism performed in an I/Q detector 66.

A current signal output circuit 67 is operatively connected to a pair of injection electrodes 68 and is configured to provide electrical current at predetermined frequencies to the injection electrodes 68. The injection electrodes 68 is configured to inject the electrical current into the body tissue, wherein the electrical current is passed from one of the injection electrodes to the other of the injection electrodes through the body. The current signal output circuit 67 is configured to provide the injected current at a plurality of frequencies in a range between 1 kHz to 3 MHz, and preferably within a range between 1.5 kHz and 2.5 MHz, and more preferably in a range between 1.90 kHz and 2 MHz. In embodiments of the present invention, the frequencies are 1.95 kHz, 3.9 kHz, 7.8125 kHz, 15.625 kHz, 31.25 kHz, 62.5 kHz, 125 kHz, 250 kHz, 500 kHz, 1 MHZ and 2 MHz.

A pair of sensing electrodes 69 is configured to detect the resulting voltage caused by the current flowing between the pair of injection electrodes 68 and through the body tissue. The sensing electrodes 69 are operatively connected to the detector 66, which receives the sensed voltage. The detector 66 comprises circuit for generating sinusoidal current waveform 70, amplifying circuits 71 for amplifying sensed voltage, multiplier 72 for multiplying the voltage with I/Q reference signals and low pass filter circuit 73 for low pass filtering the signals. The detector 66 has one path to extract the I- and Q-components of the signal. The result of the I/Q demodulation is a DC signal, which entails that the extraction of the I and Q components can be performed when required. This is in contrast to prior art I/Q demodulation in communication systems, where phase and amplitude change over time and the processing therefore has to be performed in parallel.

A control and calibration circuit 75 is operatively connected to the microcontroller 61, current frequency generation circuit 65, the current signal output circuit 67 and the detector 66. The control and calibration circuit 75 is configured to control and/or calibrate the different circuits and to communicate with the microcontroller 61.

Figure 7:
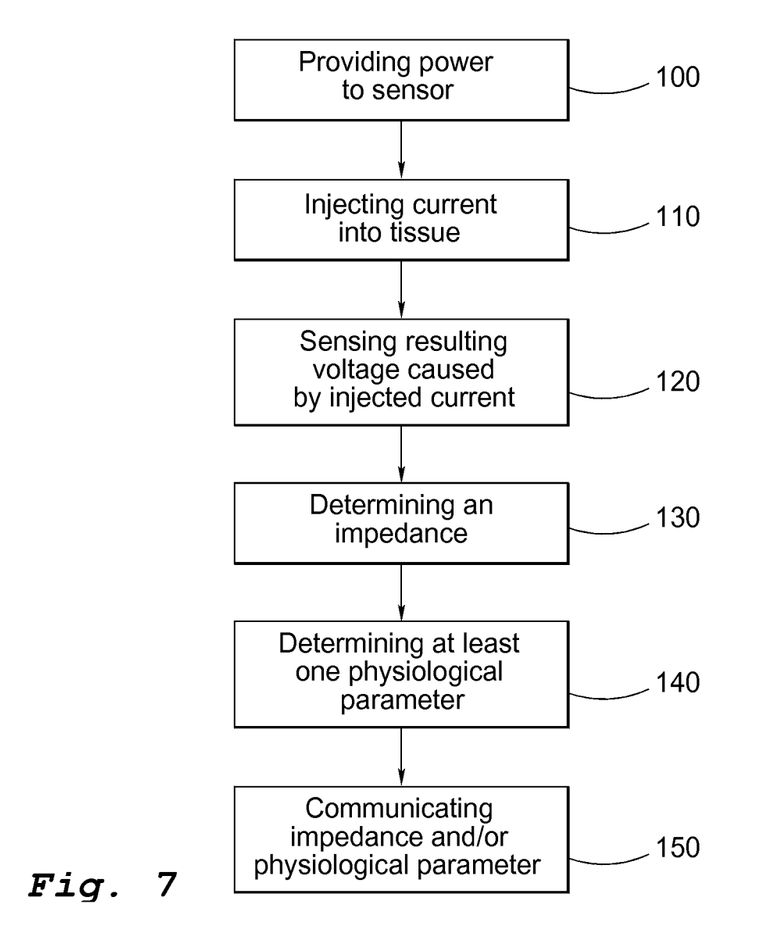
FIG. 7 is a schematic flow diagram of an embodiment of the method according to the present invention.

According to embodiments of the present invention, there is provided a method for measuring impedance in a subject using a device being configured to be implanted within the body of the subject and being configured to measure impedance within a body tissue of the subject resulting from an electrical current flowing through the body tissue, wherein the body tissue is sub-dermal or subcutaneous tissue of the subject. The method comprises on a general level the following steps:

providing, 100, power for the impedance measurement by receiving power at a coil via an electromagnetic field produced by an external coil;

injecting, 110, electrical current into the body tissue via one pair of injection electrodes, wherein the electrical current is passed from one of the injection electrodes to the other of the injection electrodes through the body;

sensing, 120, the resulting voltage caused by the current flowing between the pair of injection electrodes and through the body tissue at one pair of sensing electrodes;

measuring or determining, 130, the impedance of the body tissue based on the voltage detected by the pair of sensing electrodes.

According to embodiments of the method according to the present invention, an I/Q (In-phase/Quadrature) demodulation is performed in the step of measuring 130 on one signal path for extraction of the I and Q components, respectively, wherein a sensed voltage is received from the sensing electrodes as input and an output of the I/Q demodulation is at least one DC signal.

According to embodiments of the method according to the present invention, the method further comprises determining or monitoring 140 at least one physiological parameter of the body of the subject by correlating the measured impedance with a predetermined relationship between impedance and at least one physiological parameter.

According to embodiments of the method according to the present invention, the step of monitoring 140 at least one physiological parameter comprises determining a glucose level in the subject by correlating the measured impedance with a predetermined relationship between impedance and blood glucose levels.

According to embodiments of the method according to the present invention, the method further comprises communicating 150 the measured impedance and/or a determined value of the physiological parameter (such as a glucose level) to an external device via the coil using electromagnetic fields. If the measured impedance is communicated to the external device, the determination of the physiological parameter can be performed in the external device and the step of communicating 150 is executed before the step of determining 140 at least one physiological parameter.

According to embodiments of the method according to the present invention, the at least one physiological parameter include body temperature, hydration levels, hormone levels, lactate levels, pH, pO2, other specific ions or molecules, local pressure inside brain or scull According to embodiments of the method according to the present invention, the step of providing, 130, electrical current at predetermined frequencies to the injection electrodes comprises providing current for the injection electrodes at a plurality of frequencies in a range between 1 kHz to 3 MHz, and preferably within a range between 1.5 kHz and 2.5 MHz, and more preferably in a range between 1.90 kHz and 2 MHz.

According to embodiments of the method according to the present invention, further comprises generating reference signals having a frequency between 5 kHz to 50 MHz, an preferably in a range between 10 kHz to 20 MHz and more preferably in a range between 16 kHz to 16 MHz for the I/Q demodulation.

Figure 8:
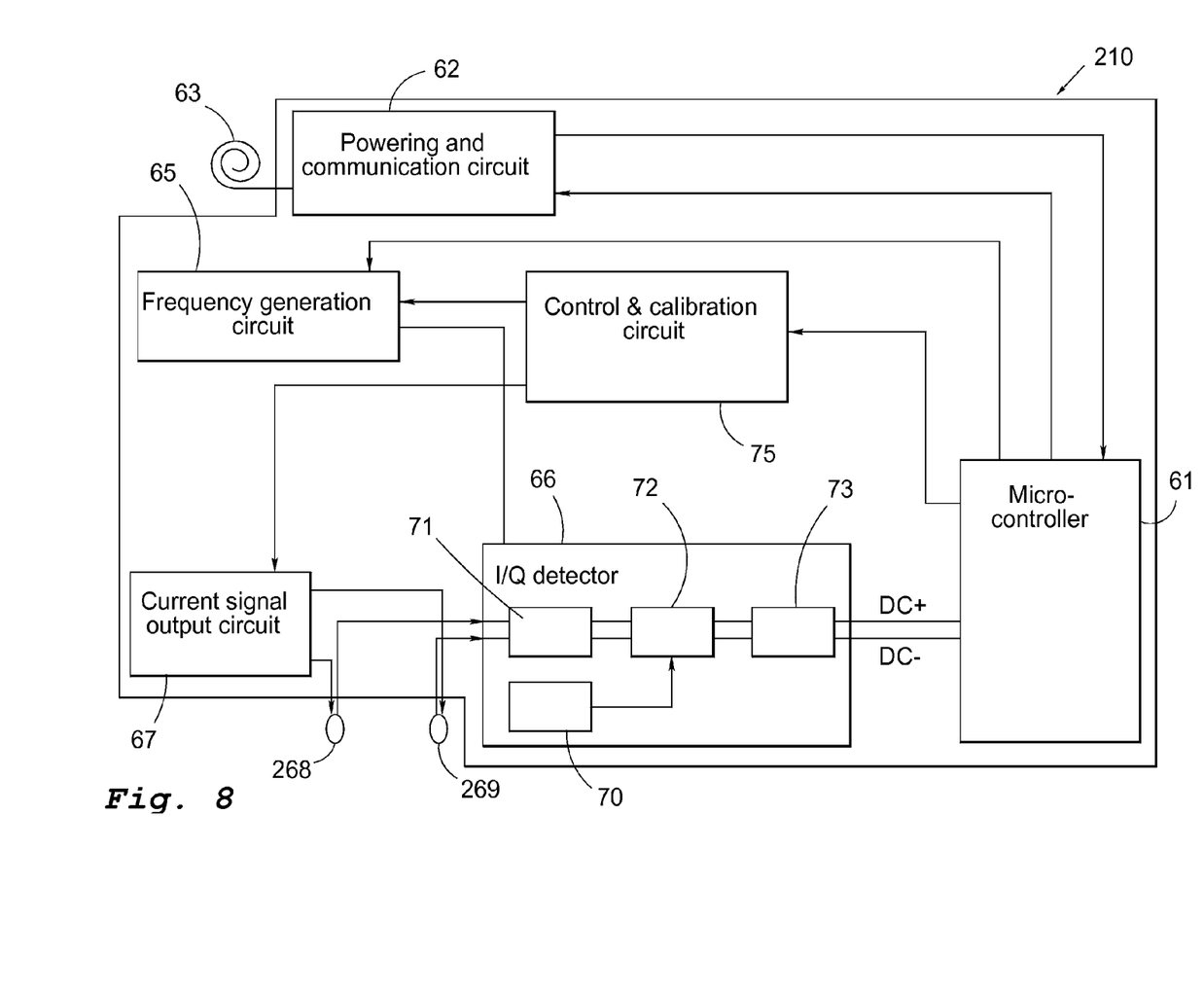
FIG. 8 is a schematic view of a further embodiment of the implantable impedance sensor according to the present invention.

With reference now to FIG. 8, another embodiment of the implantable impedance device or impedance sensor according to the present invention will be discussed in more detail. FIG. 8 shows a block diagram of this embodiment of the sensor according to the present invention.

A powering and communication circuit 62 comprising analog circuits provides power to the sensor 210. The powering and communication circuit comprises a coil 63 for external powering by the reader module 14 using inductive coupling and the powering and communication circuit 62 is also configured to establish a communication mechanism with the reader module 14 using, for example, half duplex back-scattering serial technique. The powering and communication circuit 62 includes a full-wave rectifier circuit 64 which resonates with the coil 63, for example, at frequencies in a range between 10-15 MHz. The input to the powering and communication circuit 62 is an electromagnetic field produced by the coil 13 of the reading module 14. Output of the powering and communication circuit 62 is a DC voltage. The powering and communication circuit 62 is operatively connected to the microcontroller 61.

A frequency generation circuit 65 is configured to generate frequency reference clocks from signals having a frequency between 5 kHz to 50 MHz, and preferably in a range between 10 kHz to 20 MHz and more preferably in a range between 16 kHz to 16 MHz. These frequencies are used to generate sinusoidal current and I/Q waveforms for the I/Q impedance detection mechanism performed in an I/Q detector 66.

A current signal output circuit 67 is operatively connected to a pair of electrodes 268 and is configured to provide electrical current at predetermined frequencies to the electrodes 268. The electrodes 268 are configured to inject the electrical current into the body tissue, wherein the electrical current is passed from one of the electrodes 268 to the other of the electrodes 268 through the body. The current signal output circuit 67 is configured to provide the injected current at a plurality of frequencies in a range between 1 kHz to 3 MHz, and preferably within a range between 1.5 kHz and 2.5 MHz, and more preferably in a range between 1.90 kHz and 2 MHz. In embodiments of the present invention, the frequencies are 1.95 kHz, 3.9 kHz, 7.8125 kHz, 15.625 kHz, 31.25 kHz, 62.5 kHz, 125 kHz, 250 kHz, 500 kHz, 1 MHZ and 2 MHz.

The resulting voltage caused by the current flowing between the pair of electrodes 268 and through the body tissue is detected at the electrodes 268. The electrodes 69 are also operatively connected to the detector 66, which receives the sensed voltage. The detector 66 comprises circuit for generating sinusoidal current waveform 70, amplifying circuits 71 for amplifying sensed voltage, multiplier 72 for multiplying the voltage with I/Q reference signals and low pass filter circuit 73 for low pass filtering the signals.

The detector 66 has one path to extract the I- and Q-components of the signal. The result of the I/Q demodulation is a DC signal, which entails that the extraction of the I and Q components can be performed when required. This is in contrast to prior art I/Q demodulation in communication systems, where phase and amplitude change over time and the processing therefore has to be performed in parallel.

A control and calibration circuit 75 is operatively connected to the microcontroller 61, current frequency generation circuit 65, the current signal output circuit 67 and the detector 66. The control and calibration circuit 75 is configured to control and/or calibrate the different circuits and to communicate with the microcontroller 61.

The features of the different embodiments of the sensor, method and system disclosed above may be combined in various possible ways providing further advantageous embodiments.

The invention shall not be considered limited to the embodiments illustrated, but can be modified and altered in many ways by one skilled in the art, without departing from the scope of the appended claims.

We claim:

1. A health monitoring system for determining glucose levels in a subject, the system comprising:
   an implantable sensor configured to measure impedance within a body tissue of the subject resulting from an electrical current flowing through said body tissue using a first pair of injecting electrodes and a second pair of sensing electrodes, the electrodes of the first pair of injecting electrodes and electrodes of the second pair of sensing electrodes being arranged physically separated and at a distance from one another in a row, the second pair of sensing electrodes being arranged in between the first pair of injecting electrodes, wherein current is injected into body tissue from the first pair of electrodes, the injection electrodes, and flows through the body tissue thereby causing a voltage between the second pair of electrodes, the sensing electrodes, wherein the body tissue is sub-dermal or subcutaneous tissue of said subject, the sensor including:
   a current signal output circuit operatively connected to a microcontroller and the injection electrodes and being configured to provide electrical current at predetermined frequencies to the injection electrodes,
   a detector operatively connected to the second pair of sensing electrodes and configured to receive a voltage detected by the second pair of sensing electrodes, wherein the detector is configured to measure the impedance of the body tissue based on the current flowing through the tissue between the first pair of injection electrodes and the voltage detected by the second pair of sensing electrodes,
   wherein the current signal output circuit and the first pair of injecting electrodes constitute a separate circuit from the second pair of sensing electrodes and the detector,
   the microcontroller being operatively connected to the detector and being configured to receive impedance signals from the detector and to provide control signals to the current signal output circuit,
   a powering and communication circuit having a coil configured to be powered by an electromagnetic field and to communicate with external devices;

wherein the system further includes:
   a reader module including a coil configured to produce the electromagnetic field for powering the powering and communication circuit of the sensor and for communicating with the powering and communication circuit, the coil is connected to a power generator configured to generate current and voltage for the electromagnetic field, the reader module being configured to receive transmitted data from the sensor;
   a computing device comprising a display device, a processing device and at least one storage device, the computing device being configured to communicate with other devices via at least one wireless network and to monitor at least one physiological parameter based on measured impedance, wherein the reader module and the computing device are configured to communicate with each other;
   wherein the monitoring system is configured to determine a glucose level in the subject by correlating the measured impedance with a predetermined relationship between impedance and blood glucose levels;
   and wherein said detector is a I/Q (In-phase/Quadrature) demodulator consisting of one signal path for extraction of both the I and Q components, wherein a sensed voltage is received from said sensing electrodes as input and an output of said I/Q demodulator is at least one DC signal.

2. The health monitoring system according to claim 1, further comprising a health care provider unit comprising a health care provide server, wherein said computing device comprises a medical system communication engine configured to communicate with the health care provide server via at least one wireless network.

3. The health monitoring system according to claim 2, wherein the health care provider unit comprises a patient portal, wherein a user can access patient information via the patient portal.

4. The health monitoring system according to claim 1, wherein a monitoring engine is implemented in at least one storage device of the reader module or the processing device of the computing device.

5. The health monitoring system according to claim 1, wherein the reader module is connectable to the computing device or is implemented in the computing device.

6. The health monitoring system according to claim 1, wherein the computing device is configured to display the at least one physiological parameter on the display device or a second display device of the reader module.

7. The health monitoring system according to claim 4, wherein the monitoring engine comprises an alert function configured to provide at least one alert signal when at least one monitored physiological parameter satisfy predetermined conditions.

8. The health monitoring system according to claim 4, wherein the monitoring engine comprises an information provider module configured to obtain information related to the subject from at least one device via the at least one network and to present information related to the subject on the display device of the computing device or the display device of the reader module.

9. The health monitoring system according to claim 4, wherein the monitoring engine is configured to correlate the measured impedance with the predetermined relationship between impedance and blood glucose levels.

10. The health monitoring system according to claim 1, wherein the powering and communication circuit comprises a full-wave rectifier resonating with the coil and being configured to communicate with the reading module comprising the coil via electromagnetic fields.

11. A health monitoring system according to claim 1, wherein the detector further comprises a low pass filter circuit.

12. A method of using a health monitoring system according to claim 1, comprising the step of integrating the sensor in an artificial organ, which is grown so that the sensor forms an integrated part of a full grown artificial organ after implantation of the artificial organ.

13. A health monitoring system comprising:
   an implantable sensor configured to measure impedance within a body tissue of the subject resulting from an electrical current flowing through said body tissue using a first pair of injecting electrodes and a second pair of sensing electrodes separated from the first pair of electrodes, the electrodes of the first pair of injecting electrodes and electrodes of the second pair of sensing electrodes being arranged physically separated and at a distance from one another in a row, the second pair of sensing electrodes being arranged in between the first pair of injecting electrodes, wherein current is injected into body tissue from the first pair of electrodes, the injection electrodes, and flows through the body tissue thereby causing a voltage between the second pair of electrodes, the sensing electrodes, wherein the body tissue is sub-dermal or subcutaneous tissue of said subject, the sensor including:
   a current signal output circuit operatively connected to a microcontroller and the injection electrodes and being configured to provide electrical current at predetermined frequencies to the injection electrodes,
   a detector operatively connected to the second pair of sensing electrodes and configured to receive a voltage detected by the second pair of sensing electrodes, wherein the detector is configured to measure the impedance of the body tissue based on the current flowing through the tissue between the pair of injection electrodes and the voltage detected by the second pair of sensing electrodes,
   wherein the current signal output circuit and the first pair of injecting electrodes constitute a separate circuit from the second pair of sensing electrodes and the detector, the microcontroller being operatively connected to the detector and being configured to receive impedance signals from the detector and to provide control signals to the current signal output circuit,
   a powering and communication circuit having a coil configured to be powered by an electromagnetic field and to communicate with external devices; wherein the system further includes:
   a reader module including a coil configured to produce the electromagnetic field for powering the powering and communication circuit of the sensor and for communicating with the powering and communication circuit, the coil is connected to a power generator configured to generate current and voltage for the electromagnetic field, the reader module being configured to receive transmitted data from the sensor;
   a computing device comprising a display device, a processing device and at least one storage device, the computing device being configured to communicate with other devices via at least one wireless network and to monitor at least one physiological parameter based on measured impedance, wherein the reader module and the computing device are configured to communicate with each other;

wherein the sensor is integrated in an artificial organ, which is grown so that the sensor forms an integrated part of a full grown artificial organ after implantation of the artificial organ;

and wherein said detector is a I/Q (In-phase/Quadrature) demodulator consisting of one signal path for extraction of both the I and Q components, wherein a sensed voltage is received from said sensing electrodes as input and an output of said I/Q demodulator is at least one DC signal.

* * * * *